United States Patent [19]

Maruyama et al.

[11] Patent Number: 4,735,778
[45] Date of Patent: Apr. 5, 1988

[54] MICROTITER PLATE

[75] Inventors: Nobuo Maruyama; Yoichi Shibata; Teruaki Sekine, all of Tokyo, Japan

[73] Assignee: Kureha Kagaku Kohyo Kabushiki Kaisha, Tokyo, Japan

[21] Appl. No.: 899,039

[22] Filed: Aug. 22, 1986

[30] Foreign Application Priority Data

Aug. 28, 1985 [JP] Japan .................................. 60-187352
Aug. 28, 1985 [JP] Japan .......................... 60-130041[U]

[51] Int. Cl.⁴ .............................................. B01L 3/00
[52] U.S. Cl. ..................................... 422/102; 435/301; 436/809
[58] Field of Search ................... 422/65, 72, 102, 104; 436/809; 206/328, 334; 435/299–301

[56] References Cited

U.S. PATENT DOCUMENTS

| 3,494,459 | 2/1970 | Wallestad | 206/328 |
| 4,146,365 | 3/1979 | Kay et al. | 436/809 |
| 4,154,795 | 5/1979 | Thorne | 422/102 |
| 4,292,273 | 9/1981 | Butz et al. | 422/102 |
| 4,483,442 | 11/1984 | Worth | 206/328 |
| 4,501,719 | 2/1985 | Williams | 436/809 |
| 4,527,677 | 7/1985 | March et al. | 206/334 |
| 4,615,927 | 10/1986 | Holzmann | 206/328 |

Primary Examiner—Michael S. Marcus
Attorney, Agent, or Firm—Robert F. Ziems

[57] ABSTRACT

A microtiter plate is made of a light-transmitting antistatic resin and defines at least one well. The bottom wall of the well is centrally equipped with a flat portion having a diameter of at least 1 mm and is preferably connected continuously to the corresponding peripheral wall by way of a rising part. The minimum radius of curvature of the inner wall of said well, said inner wall including said rising part, is preferably at least 0.5 mm.

6 Claims, 2 Drawing Sheets

MICROTITER PLATE

BACKGROUND OF THE INVENTION

(1) Field of the Invention

This invention relates to a microtiter plate suitable for use, for example, in reacting liquid portions each of which is of a minute quantity.

(2) Description of the Prior Art

It is now known to conduct the detection or measurement of a component contained in a liquid sample or reagent of a minute quantity by placing the liquid sample or reagent in a well of a microtiter plate, inducing a chemical reaction, biological reaction or the like, which is accompanied by color development or discoloration, in the liquid sample or reagent and then determining results of the reaction by optical means, namely, by projecting a beam of light onto the resultant reaction mixture in the well and measuring the intensity of light transmitted therethrough. Since this method requires the sample or reagent only in a minute quantity (usually, less than 1 cc), it is applied widely for the inspection of water quality, the diagnoses of diseases based on blood samples and other purposes.

In a method of the above-mentioned sort, it is generally required to divide each sample into many portions and then to react the resulting sample portions with many reagents of different kinds respectively so that the same sample can be tested with respect to many items. As an alternative, it is also required to react many samples with the same reagent so that the same test can be performed on such many samples. In order to carry out such reactions efficiently, microtiter plates such as that shown in FIG. 3 have conventionally been used. In FIG. 3, a microtiter plate 20 is made of a transparent material and defines a number of round-bottomed reaction wells 10 equipped with openings 11. Each of the reaction wells 10 may be adapted as a reaction vessel. A liquid sample or reagent is dropped from an automatic buret into each reaction well 10. After completion of a prescribed reaction or treatment, results of the reaction or treatment are detected by optical means.

The procedures for the reaction of a liquid of a minute quantity and the subsequent detection of results of the reaction, which make use of such a microtiter plate as described above, are however accompanied by a variety of serious problems as a matter of fact. For example, a beam of light the spot diameter of which is about 2 mm is usually employed in the procedure for the detection of results of the reaction. However, detection results obtained vary significantly and do not have sufficiently high reliability. For these reasons, information obtained by such a method as described above has a low value only. Its merit cannot therefore be utilized fully although the method itself is excellent.

SUMMARY OF THE INVENTION

It has practically been unknown why detection results obtained by such a method as described above vary to a significant extent. As a result of various investigation, the following causes were found as some of important causes:

(a) A liquid which undergoes a reaction is not always placed centrally on the bottom wall of a reaction well.

(b) Although a high degree of positional accuracy is required for an optical measuring instrument, this requirement is not satisfied due to the configurations of the reaction well.

(c) Microtiter plates, in each of which each reaction well is cylindrical with a flat bottom wall and the bottom wall and cylindrical wall extend at a right angle, have also been employed to date. In a washing operation required in each reaction step, these microtiter plates do not facilitate their washing at the corners between the bottom walls and cylindrical walls of their reaction wells so that insufficient washing tends to occur there.

Further, these conventional microtiter plates are generally made of a resin such as polyvinyl chloride resin, polystyrene or an acrylic resin and are hence very susceptible to static electrification. Due to this static electrification of microtiter plates, dropped reagents may be scattered around, in other words, may be subjected to static atomization. Under the influence of static attraction produced by this static electrification, reactions may proceed while reactants are not properly positioned or are kept in adherence on side walls. Accurate detection results may hence not be obtained in many instances.

The present inventors have proceeded with a further investigation on such deleterious causes in various ways. As a result, the present invention has now been completed.

In one aspect of this invention, there is thus provided a microtiter plate characterized in that said plate defines at least one well, the bottom wall of said well centrally includes a flat portion having a diameter of at least 1 mm and said plate is made of a light-transmitting antistatic resin.

A microtiter plate of such a structure as described above can satisfy conditions which are required for performing detection by optical detection means without failure in actual procedures for a reaction of a liquid of a minute quantity and detection of reaction results. It is hence always possible to obtain consistent and highly reliable detection results.

The above and other objects, features and advantages of the present invention will become apparent from the following description and the appended claims, taken in conjuction with the accompanying drawings.

DETAILED DESCRIPTION OF THE INVENTION AND PREFERRED EMBODIMENTS

Figure 1:
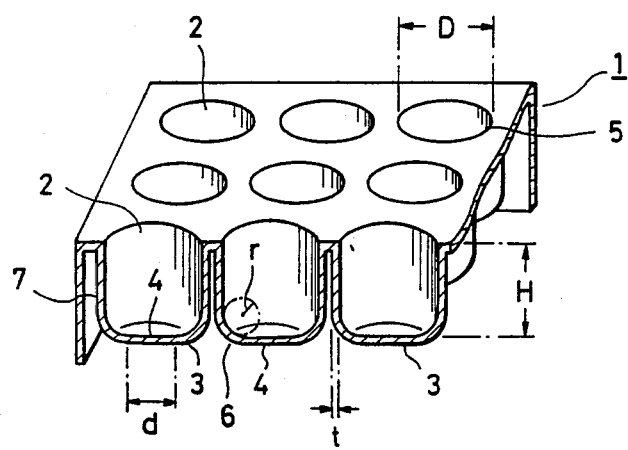
FIG. 1 is an enlarged fragmentary perspective view of a microtiter plate according to one embodiment of this invention, some parts of which are shown in cross-section.
Figure 3:
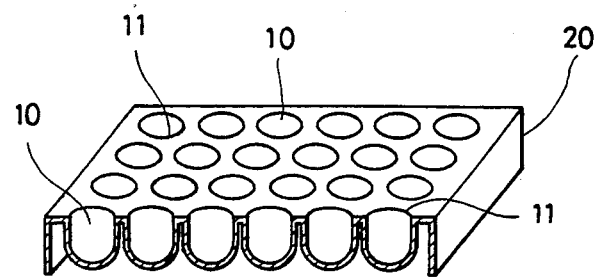
FIG. 3 is a perspective view of a conventional microtiter plate, some parts of which are shown in cross-section.

Referring first to FIG. 1, a microtiter plate 1 is made of a light-transmitting antistatic resin and defines a plurality of reaction wells 2. In each of the wells 2, a flat part 4 having a diameter of at least 1 mm is formed centrally in a bottom wall 3. The inner surface of the bottom wall 3 of the well 2 and the inner surface of its peripheral wall 7 are connected continuously by way of a smooth arcuate surface so as to avoid formation of any corners. Specifically, it is preferable to connect the bottom wall 3 continuously to the peripheral wall 7 by way of a rising part 6 the inner surface of which has a radius r of curvature of at least 0.5 mm.

In the above embodiment, the following specific dimensions may be given by way of example in order to illustrate the configurations of each well 2.

Diameter D of an opening 5: 7 mm
Depth H of the well 2: 11 mm
Diameter d of the flat part 4: 5 mm
Thickness t of the bottom wall 3: 0.7 mm Such wells 2 are arranged in rows and columns.

Figure 2:
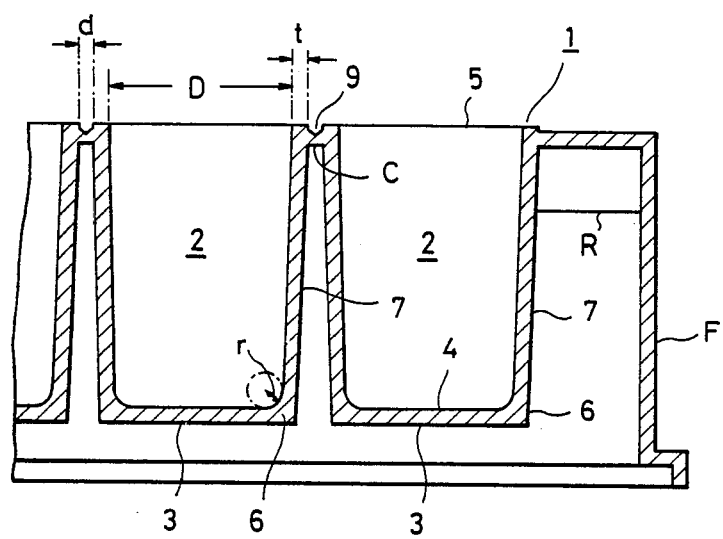
FIG. 2 is an enlarged fragmentary cross-sectional view of a microtiter plate according to another embodiment of this invention.

Referring next to FIG. 2 which illustrate another embodiment of this invention, each of reaction wells 2 arranged in rows and columns is formed of a bottom wall 3 and a peripheral wall 7. The bottom wall 3 has a flat plate-like shape while the peripheral wall 7 has a conical shape which slightly flares upwards. The peripheral edge of the bottom wall 3 is connected continuously to the peripheral wall 7 by way of a rising part 6. The radius r of curvature of the inner surface of the rising part 6 is set at 0.5 mm or greater. The entire inner surface of the well 2 does not contain any part the radius of curvature of which is smaller than 0.5 mm.

Letter C indicates a connecting part between two wells 2 located side by side, for example, in the lateral direction. The thickness of this connecting part C is set, for example, at 0.7 mm and the upper surface of the connecting part C defines a so-called V-shaped groove 9 in the longitudinal direction of the microtiter plate 1 (i.e., in the direction perpendicular to the drawing sheet). On the other hand, each two adjacent wells which are positioned side by side in the longitudinal direction may also be connected together by a connecting part similar to the connecting part or by providing a reinforcing rib additionally.

Designated at letter F is an outer side wall of the microtiter plate 1, which also serves as a stand. Letter R indicates the reinforcing rib.

In this embodiment, the following specific dimensions may be given by way of example.

Thickness t of the bottom wall 3 and peripheral wall 7: 0.7 mm
Opening diameter D of the wells 2: 7 mm
Diameter of flat parts 4: 4 mm
Radius r of curvature: 1.0 mm
Width d of the connecting parts C: 0.6 mm
Minimum thickness of the connecting parts C at the V-grooves 9: 0.35 mm In order to ensure identification of the wells 2, it is preferred to form certain identification marks in association with the individual wells 2. As such identification marks, it may for example be convenient to combine letters of the Roman alphabet in the order of A, B, C, . . . , which indicate columns, and numbers in the order of 1, 2, 3 . . . which designate rows so that the addresses of the wells can be indicated as "A1" for the well in the first column and first row and "C5" for the well in the third column and fifth row.

On the other hand, as the light-transmitting antistatic resin useful as a material for the microtiter plate of this invention, it is preferable to use a graft copolymer obtained by graft-polymerizing at least one ethylenically-unsaturated monomer on a rubber-like backbone polymer which contains, as a constituent thereof, a monomer having an alkylene oxide group and an ethylenically-unsaturated bond. Specifically, it may be important that the antistatic resin has such antistatic property as 30 seconds or shorter, preferably, 10 seconds or shorter in terms of the halflife of static surface electrification as measured by a static charge gauge, for example, "Static Honest Meter" (trade mark; manufactured by Shishido Shokai K.K.) and such a high light transmittance as 80% or higher, preferably, 87% or higher in terms of the transmittance of whole light. Incidentally, this transmittance of whole light can be measured, for example, by the method prescribed in JIS K6717.

The microtiter plate of this invention may take any specific configurations so long as the above-described conditions are met. It is supposed to contain at least one reaction well for reception of a liquid. Where two or more wells 2 are provided, the size of each of the wells 2 may usually be about 3–30 mm in diameter and about 2–15 mm in depth. In the microtiter plate of this invention, its wall may take a multi-layered structure provided that the surface layer is made of an antistatic resin.

In the present invention, it is preferable to form the microtiter plate by using, as its material namely as an antistatic resin, a resin composed of a specific graft copolymer. The resin may be composed solely of the graft copolymer or may be a mixture of the graft copolymer and a thermoplastic resin. The term "specific graft copolymer" as used herein means a graft copolymer obtained by graft-polymerizing at least one ethylenically-unsaturated monomer on a rubber-like backbone polymer which contains, as a constituent thereof, a monomer having an alkylene oxide group and an ethylenically-unsaturated bond.

Specifically, the rubber-like backbone polymer may preferably be a rubber-like copolymer obtained from 50–90 wt. % of at least one monomer selected from conjugated dienes and acrylic esters and 10–50 wt. % of a monomer containing 4–500 alkylene oxide groups and ethylenically-unsaturated bonds (hereinafter called "polyalkylene oxide monomer") and if necessary, 0–50 wt. % of at least one ethylenically-unsaturated copolymerizable monomer.

The above-described rubber-like backbone polymer may be composed principally of said at least one monomer selected from the conjugated dienes and acrylic esters. As the conjugated dienes, 1,3-butadiene, isoprene, chloroprene an 1,3-pentadiene may be used. As useful acrylic esters, may be mentioned ethyl acrylate, propyl acrylate, butyl acrylate, hexyl acrylate, octyl acrylate, nonyl acrylate and so on.

By using a conjugated diene and an acrylic ester either singly or in combination in a total amount of at least 50 wt. % based on the rubber-like backbone polymer, the glass transition temperature of the rubber-like backbone polymer can be lowered significantly and remarkable antistatic effects can be brought about. Unless this proportion is 90 wt. % or smaller, the proportion of the polyalkylene oxide monomer is reduced and the intended antistatic effects may hence not be obtained.

The polyalkylene oxide monomer includes one or more alkylene oxide blocks each of which is bonded to an ethylenically-unsaturated group and is represented by the following formula:

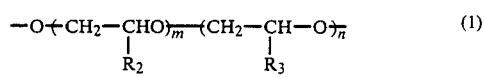
(1)

wherein $R_2$ and $R_3$ may be the same or different and mean individually a hydrogen or an alkyl group having 1-4 carbon atoms, and m and n stand for integers satisfying $4 \leq m+n \leq 500$. Particularly preferred is a polyalkylene oxide monomer having ethylene oxide blocks each of which contains 4 or more ethylene oxide groups of the above formula (1) in which at least one of $R_2$ and $R_3$ is H.

As the polyalkylene oxide monomer on the other hand, at lest one monomer represented by the following structural formula (2) or (3) is preferred.

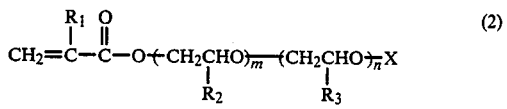
(2)

wherein $R_1$ is a hydrogen atom or an alkyl group having 1—4 carbon atoms, X means a hydrogen atom, alkyl group having 1-9 carbon atoms, phenyl group, $SO_3Me$, $SO_2Me$, $PO_3Me_2$,

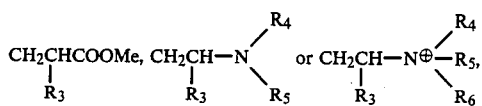

$R_4$, $R_5$ and $R_6$ denote individually a hydrogen atom or alkyl group having 1-9 carbon atoms, Me stands for a hydrogen, Na, Li or K atoms, and $R_2$, $R_3$, m and n have the same meaning as defined above in the formula (1).

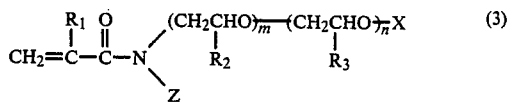
(3)

wherein Z means a hydrogen atom, alkyl group having 1-40 carbon atoms, cycloalkyl group having 3-6 carbon atoms, phenyl group or

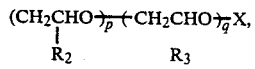

p and q stand for integers satisfying $4 \leq p+q \leq 500$, and $R_1$, $R_2$, $R_3$ and X have the same meaning as defined above in the formula (2).

Among the above-described monomers represented by the formula (2) or (3), those of the formula (2) or (3) in which at least one of $R_2$ and $R_3$ is H and 4 or more ethylene oxide groups are contained are particularly preferred.

Besides the monomers represented by the formula (2) or (3), it is of course possible to use a monomer which can lower the volume resistivity of the rubber-like backbone polymer containing ethylenically-unsaturated bonds and polyalkylene oxide groups and obtained by copolymerization with a conjugated diene and/or an acrylic acid.

The polyalkylene oxide monomer may preferably contain 4-500 alkylene oxide groups with 6-50, especially, 9-50 alkylene oxide groups being preferred. If the number of alkylene oxide groups is smaller than 4, it is difficult to obtain sufficient antistatic properties. If it is greater than 500 on the other hand, the polyalkylene oxide monomer has low solubility to water or the associated monomer upon its polymerization and moreover, its polymerizability is reduced. It is hence not preferred to contain alkylene oxide groups in any numbers outside the above range.

The rubber-like backbone polymer may preferably contain the polyalkylene oxide monomer in an amount of 10 wt. % or more, whereby sufficient antistatic properties are imparted. It is preferable to limit the proportion of the polyalkylene oxide monomer below 50 wt. %, because such a proportion facilitates its polymerization in the graft copolymerization and the post treatment of the resulting polymer such as its acidifying out, salting out or the like.

As the ethylenically-unsaturated monomer which is copolymerizable with a conjugated diene or acrylic ester and may be used upon production of the rubber-like backbone polymer as needed, conventionally-known monomers may be used.

For example, one or more of the following monomers may be used: alkyl acrylates, alkyl methacrylates, acrylic acid, methacrylic acid, acrylamide, methacrylamide, vinyl acetate, unsaturated nitriles, aromatic vinyl compounds, alkyl vinyl ethers, alkyl vinyl ketones, 2-hydroxyethyl acrylates, 2-hydroxyethyl methacrylates, diacetone acrylamide, vinyl chloride, vinylidene chloride, itaconic acid, alkyl itaconates, isobutene, 2-acidphosphoxyethyl methacrylate, 3-chloro-2-acid-phosphoxypropyl methacrylate, sodium styrenesulfonate, etc.

Still better antistatic properties may be obtained if a high-polarity monomer such as acrylonitrile or a monomer containing one or more anionic substituents such as sulfonic, phosphoric and/or carboxylic groups is chosen as the above-mentioned ethylenically-unsaturated copolymerizable monomer.

These ethylenically-unsaturated copolymerizable monomers may each be used in an amount up to 50 wt. % in the rubber-like backbone polymer. If it is used beyond this upper limit, the glass transition temperature becomes higher and rubber-like characteristics are hence lost.

It is also feasible to use, if necessary, a polyfunctional monomer containing one or more ethylenically-unsaturated groups such as vinyl, 1,3-butadienyl, acryl, methacryl and/or allyl groups as a crosslinking agent in the rubber-like backbone polymer. A polyfunctional monomer containing additional 4-500, preferably, 9-50 polyalkylene glycol groups is particularly preferred, because it acts not only as a crosslinking agent but also as a antistatic agent.

As an ethylenically-unsaturated monomer to be graft copolymerized on such a rubber-like backbone polymer, one or more conventionally-known monomers may be used. For example, the following monomers may be used either singly or in combination: alkyl acrylates, alkyl methacrylates, acrylic acid, methacrylic acid, acrylamide, methacrylamide, vinyl acetate, unsaturated nitriles, aromatic vinyl compounds, conjugated dienes, alkyl vinyl ethers, alkyl vinyl ketones, 2-hydroxyethyl (meth)acrylates, (alkoxy)polyethylene glycol (meth)acrylates, diacetone acrylamide, vinyl chloride, vinylidene chloride, itaconic acid, alkyl itaconates, isobutene and the like.

The proportions of the rubber-like backbone polymer and branch polymer in the graft copolymer may be 5-95 wt. %, preferably, 8-80 wt. % for the former and 5-95 wt. %, preferably, 20-92 wt. % for the latter. If the rubber-like backbone polymer is contained in any amount smaller than 5 wt. %, it is difficult to impart antistatic properties. On the other hand, any proportions greater than 95 wt. % result in loss of stiffness when the resulting graft copolymers are used alone or low compatibility and difficult mixing when the resulting graft copolymers are employed as mixtures with other thermoplastic resins.

When the graft copolymer is used as a mixture in combination with a thermoplastic resin, the proportion of the rubber-like backbone polymer may be controlled within a range of 5–80 wt. %, preferably, 10–60 wt. %.

As exemplary thermoplastic resins usable together with the graft copolymer, may be mentioned polyethylene, polypropylene, polyvinyl chloride, nitrile resins, polymethyl methacrylate and their copolymers, acrylonitrile-styrene-butadiene resins, acrylonitrile-styrene resins, polyamide resins, polyester resins, fluoro carbon resins and the like. Needless to say, other thermoplastic resins may also be used so long as they have good compatibility with the graft copolymer.

The above-described resins can each be molded into microtiter plates having reaction wells by a usual injection molding or vacuum sheet forming technique.

As has been described above, the microtiter plate of this invention makes use of an antistatic resin as its material and includes one or more wells the bottom walls of which are each equipped with a flat part. It can therefore bring about the following advantageous effects.

If a microtiter plate is subjected to static electrification, a droplet of a liquid sample or reagent which one wants to fill in a desired well may not be placed there and may hence adhere on the edge of the opening of the well or the peripheral wall of the well. As a consequence, even if the bottom wall is round, the droplet may not be placed on the bottom center of the well through which center a beam of light is caused to transmit in a detection procedure. In addition, the intended reaction may be impaired as a result of deposition of dust, which is floating in the atmosphere, on the surface of the microtiter plate.

Owing to the use of an antistatic resin in the present invention, the microtiter plate is maintained free from static electrification and as a result, when a liquid sample or reagent to be charged or filled in a desired well is dropped, the droplet is allowed to fall in the desired well without failure. It is hence possible to subject a liquid of a minute quantity to an intended reaction with high efficiency and ease by means of an automatic buret.

The reaction may be an enzymatic immuno-reaction by a solid-phase technique. If well-defining portions are charged or electrified statically, the degree of conjugation of an antigen or antibody to be conjugated will be different from one well to another due to the static electricity. The microtiter plate of this invention is free of such a problem and here again, can provide highly-reliable results.

As has been described above, use of the antistatic resin as a material for the microtiter plate has made it possible to keep its individual wells under the same conditions. Besides, each droplet filled is assured to assume a position on the bottom of the intended well. Since a flat part is formed there, the thickness of the layer of the droplet on the flat part becomes uniform provided that the microtiter plate is positioned horizontally. In a detection procedure, the thickness of the liquid layer is always constant irrespective of the location through which a beam of light is caused to transmit. It is therefore possible to avoid such a problem as encountered upon use of a round-bottomed well, namely, that detection results vary depending on the location of transmission of a beam of light. By making the size of the flat part as great as at least 1 mm in terms of its diameter, it is possible to successfully tolerate errors, which generally take place in the positional accuracy of projection of a beam of light, and hence to perform detection of reaction results consistently and stably by optical means.

Furthermore, the microtiter plate is maintained free from deposition of dust in the atmosphere owing to its own antistatic properties. There is thus no danger that the intended reaction could be impaired by such impurities.

Perfect washing can be ensured by forming the microtiter plate into such a structure that the inner surface of the bottom wall of each reaction well and the inner surface of its peripheral wall are connected continuously by way of a smooth arcuate surface and formation of any corners is hence avoided. It is therefore feasible to eliminate the cause for errors due to incomplete washing. This feature is now described more specifically. When the inner surface of each well 2 does not contain any part the radius of curvature of which is smaller than 0.5 mm, it is possible to discharge a liquid, which has been filled in the well 2, smoothly and completely in its entirety, for example, by turning the whole microtiter plate up side down. Especially, the liquid is no longer allowed to remain by capillary action at the boundary between the bottom wall 3 and peripheral wall 7. The washing procedure can hence be performed always completely. As a result, it is possible to avoid the cause for errors due to incomplete washing even when the reaction requires washing as an essential step, for example, like an enzymatic immunoreaction.

When a resin composed of the above-described specific graft copolymer is used as a material for the microtiter plate in the present invention, the resin generally has excellent ion-diffusing property as one of chemical properties of the resin, in other words, high conductivity to static electricity. When the resin is used in the form of a wall or layer having at least a certain level of thickness, it is easily possible to obtain a microtiter plate having high antistatic properties, namely, having a static surface electrification halflife of 30 seconds or shorter.

As illustrated in FIG. 2, the V-grooves 9 or the like may also be formed as tear grooves in the connecting parts C. Such tear grooves may also be formed in the lateral direction in the connecting parts between longitudinally-adjacent wells 2. By tearing the connecting parts along the tear grooves by means of a cutter knife or the like, the adjacent wells 2 can be separated with extreme ease column by column or row by row. It is also extremely easy to separate a desired group of wells only. When the number of samples or test items is small and the wells in the microtiter plate are not all used at the same time, a portion of the microtiter plate in which wells of a desired number are contained is cut out so that the microtiter plate can be used conveniently without wasting same. By the way, the minimum thickness of each connecting part at its associated tear groove may preferably range from 0.2 mm to 0.5 mm although it varies depending on the material. So long as the thickness falls within such a range, the cutting is facilitated and at the same time, the connecting part can exhibit sufficient connecting strength in usual application.

Microtiter plates according to this invention can be used for various reactions, specifically, for blook tests, various enzymatic reactions, growth of antiboides, culture of microorganisms, culture of plant cells, etc.

EXAMPLE 1

(a) In a 10-l stainless steel autoclave equipped with a stirring blade, an aqueous solution having the following materials was charged subsequent to its adjustment to pH 7 with an aqueous solution of sodium hydroxide:

|  | Parts |
| --- | --- |
| 1,3-Butadiene | 12 |
| Methyl acrylate | 4 |
| Methoxypolyethylene glycol methacrylate (number of ethylene oxide groups: about 23 on average) | 4 |
| Diisopropylbenzene hydroperoxide | 0.04 |
| Formaldehyde sodium sulfoxylate | 0.02 |
| Ferrous sulfate heptahydrate | 0.0008 |
| Disodium ethylenediaminetetraacetate | 0.0012 |
| Sodium pyrophosphate | 0.01 |
| Sodium dodecylbenzenesulfonate | 0.2 |
| Deionized water | 60 |

The autoclave was purged thoroughly with nitrogen gas and the contents were stirred at 40° C. for 20 hours, thereby obtaining a rubber latex having an average particle size of 0.08 μm with a yield of 99%.

(b) To 40 parts of the above rubber latex (10 parts as a rubber-like backbone polymer), the following materials were added:

|  | Parts |
| --- | --- |
| Methyl methacrylate | 80 |
| n-Octyl mercaptan | 0.64 |
| Potassium persulfate | 0.064 |
| Sodium hydrogensulfite | 0.016 |
| Sodium dodecylbenzenesulfonate | 0.8 |
| Deionized water | 240 |

The autoclave was purged with nitrogen gas and the contents were stirred at 50° C. for 20 hours. The graft-copolymerized latex was taken out of the autoclave, followed by an addition of an aqueous solution of aluminum sulfate to deposit the thus-obtained graft copolymer. The resultant mixture was adjusted to pH 7 with an aqueous solution of sodium pyrophosphate. After the graft copolymer was dewatered and then washed, it was dried at 55° C. for 24 hours to obtain white powder with a yield of 97%.

Using the white powder as a raw material, a microtiter plate having the same structure as that shown in FIG. 1 was molded by means of a usual injection molding machine. The microtiter plate was 82 mm long, 123 mm wide, 14 mm high and 0.7 mm thick. It contained 96 wells in total, arranged in 12 rows and 8 columns. Each of the wells had the following dimensions:
Diameter: 7 mm
Depth: 11 mm
Diameter of the flat part of the bottom wall: 1.5 mm
Radius of curvature of the rising part between the bottom wall and peripheral wall 2.75 mm In an atmosphere of 23° C. and 20% R.H., the halflife of static surface electrification of the microtiter plate was 12 seconds and the transmission of whole light was 90.5%. The following measuring methods were used.
(1) Halflife:

A specimen was set on a "Static Honest Meter" (trade mark; static charge gauge manufactured by Shishido Shokai Kabushiki Kaisha) and negative electrons were charged on its surface under the following conditions:
Discharge distance: 20 mm
Voltage applied: 10 KV
Revolution speed: 1300 rpm After stopping the charge, the time required until the static electrification of its surface dropped to one half of the initial value was measured.
(2) Transmission of whole light:
The method prescribed in JIS K 6717 was followed.

Using the above-obtained microtiter plate, an enzymatic immunoreaction was also conducted. In the following description, "PBS" and "BSA" stand for a phosphate-buffered saline and bovine serum albumin respectively.

(1) A 50 μg/ml·PBS solution of anti-mouse immunoglobulin rabbit antibody was filled in an amount of 50 μl in each of the wells. The solution was then allowed to stand there at 4° C. for 24 hours to fix the antibody.

(2) After washing each well three times with PBS, a 30 mg/ml·PBS solution of BSA was charged in an amount of 150 μl to each of the wells. They were reacted at 4° C. for 24 hours.

(3) After washing each well three times with PBS, 50 μl of PBS which contained mouse immunoglobulin at a concentration of 25 ng/ml and 1% of BSA was added to each of 84 wells in 7 columns out of the 96 wells in total. To each of the 12 wells in the remaining one column, 50 μl of PBS containing 1% of BSA was added as a blank. They were reacted at room temperature for 2 hours.

(4) After washing each well five times with PBS, 50 μl of PBS which contained at a rate of 1 μg/ml anti-mouse immunoglobulin horse antibody labelled by horseradish peroxidase and 1% of BSA was added to each well. They were reacted at room temperature for 1 hour.

(5) After washing each well five times with PBS, 100 μl of a solution containing 0.01% of hydrogen peroxide in a citrate buffer of pH 5.0 which contained orthophenylene diamine at a rate of 1 mg/ml was added. They were reacted at room temperature for 20 minutes.

(6) Then, 25 μl of 2M sulfuric acid were added. On an automatic absorptiometer, a beam of light having a wavelength of 490 nm and a spot diameter of 1 mm was projected to measure the absorbance.

Measurement results obtained with respect to the 84 samples in the 7 columns were investigated. The following results were obtained.
Average value: 0.561
Standard deviation: 0.023

Accordingly, the coefficient of variation which is an index for the extent of variation was very small, i.e., 4.1. It is hence clear that microtiter plate of this Example had excellent stability and gave high reliability.

EXAMPLE 2

Molded was a microtiter plate of the same configurations as that obtained in Example 1 except that each well had the following dimensions:
Diameter of the opening: 7 mm
Depth: 11 mm
Diameter of the flat part of the bottom wall: 5 mm
Radius of curvature of the rising part: 1 mm Using the microtiter plate, measurements were conducted in the same manner as in Example 1. The following results were obtained:

Average value: 0.558
Standard deviation: 0.021

Accordingly, the coefficient of variation which is an index for the extent of variation was extremely small, i.e., 3.8. It is hence clear that microtiter plate of this Example had excellent stability and gave high reliability.

COMPARATIVE EXAMPLE 1

A microtiter plate was molded in the same manner as in Example 1 except that the diameter of the flat part in the bottom wall of each well was 0.8 mm and similar measurements were conducted. The following results were obtained.

Average value: 0.552
Standard deviation: 0.045

Accordingly, the coefficient of variation was 8.2. It is thus envisaged that the measurement results varied significantly.

COMPARATIVE EXAMPLE 2

A microtiter plate was molded in the same manner as in Example 1 except that commercial polystyrene was used as a material. Similar measurements were then conducted. The following results were obtained.

Average value: 0.596
Standard deviation: 0.038

Accordingly, the coefficient of variation was 6.4. It is hence envisaged that the measurement results varied considerably.

COMPARATIVE EXAMPLE 3

A microtiter plate was molded in the same manner a in Example 1 except that commercial polyvinyl chloride was used as a material. Similar measurements were then conducted. The following results were obtained.

Average value: 0.401
Standard deviation: 0.053

Accordingly, the coefficient of variation was 12.5. It is hence envisaged that the measurement results varied extremely.

Having now fully described the invention, it will be apparent to one of ordinary skill in the art that many modifications and changes can be made thereto without departing from the spirit or scope of the invention as set forth herein.

We claim:

1. In a microtiter plate including at least one well having a bottom wall, the improvement wherein:
   said bottom wall of said well comprises a central flat portion having a diameter of at least 1 mm and wherein said plate is made of a light-transmitting antistatic resin composed of a graft copolymer obtained by graft-polymerizing at least one ethylenically-unsaturated monomer on a rubber-like backbone polymer which contains, as a constituent thereof, a monomer having an alkylene oxide group and an ethylenically-unsaturated bond.

2. The microtiter plate as claimed in claim 1, wherein said well includes a continuous inner surface formation defined by a peripheral surface, a bottom wall surface and a curved merging surface continuously joining the peripheral surface and the bottom wall surface, and wherein the minimum radius of curvature of any portion of the inner surface formation of said well is at least 0.5 mm.

3. The microtiter plate as claimed in claim 1, wherein the halflife of the static surface electrification of said antistatic resin as measured by a static charge gauge is 30 seconds or shorter and the transmittance of whole light through said antistatic resin is 80% or higher.

4. The microtiter plate as claimed in claim 1, wherein the microtiter plate contains a plurality of wells arranged in a pattern of rows and columns and has tear grooves formed between at least adjacent rows of the wells.

5. In a microtiter plate having at least one well, the improvement comprising:
   said plate is made of a light-transmitting antistatic resin composed of a graft copolymer obtained by graft-polymerizing at least one ethylenically-unsaturated monomer on a rubber-like backbone polymer which contains, as a constituent thereof, a monomer having an alkylene oxide group and an ethylenically-unsaturated bond.

6. The microtiter plate as claimed in claim 5, wherein the halflife of the static surface electrification of said antistatic resin as measured by a static charge gauge is 30 seconds or shorter and the transmittance of whole light through said antistatic resin is 80% or higher.

* * * * *